US00RE39892E

(19) United States
(12) Reissued Patent
De Simone

(10) Patent Number: US RE39,892 E
(45) Date of Reissued Patent: Oct. 23, 2007

(54) PHARMACEUTICAL COMPOSITIONS CONTAINING LACTOBACILLI FOR TREATMENT OF VAGINAL INFECTIONS AND RELATED METHOD

(76) Inventor: Claudio De Simone, Via Fabretti, 8, 00161 Rome (IT)

(21) Appl. No.: 11/484,028

(22) Filed: Jul. 11, 2006

Related U.S. Patent Documents

Reissue of:
(64) Patent No.: 6,277,370
Issued: Aug. 21, 2001
Appl. No.: 09/185,572
Filed: Nov. 4, 1998

(30) Foreign Application Priority Data

Apr. 30, 1998 (EP) ..... 98830264

(51) Int. Cl.
*C12N 1/20* (2006.01)

(52) U.S. Cl. ..... 424/93.45
(58) Field of Classification Search ..... None
See application file for complete search history.

(56) References Cited

U.S. PATENT DOCUMENTS 4,591,499 A * 5/1986 Linn et al. ..... 424/93.45
5,705,160 A * 1/1998 Bruce et al. ..... 424/93.45

FOREIGN PATENT DOCUMENTS

EP 0 353 581 * 2/1990
GB 2 261 372 * 5/1993
HU 214 991 * 1/1991
HU 960 182 * 4/1996
WO 94/06416 * 3/1994
WO 95/33046 * 12/1995
WO 96/38159 * 12/1996

OTHER PUBLICATIONS

Giorgi et al., "Identification of vaginal lactobacilli from asymptomatic women", Microbiologica (Bologna) 10 (4) : 377–384 (1987).*
Dembele et al., "Inhibition of Bacterial Pathogens by Lacotbacilli", Zent.bl. Bakteriol. 288 : 395–401 (1998).*
ATCC Catalog of Bacteria and Bacteriophages, 19$^{th}$ Ed. p. 198 (1996).*

* cited by examiner

*Primary Examiner*—Sandra E. Saucier
(74) *Attorney, Agent, or Firm*—Morgan Lewis & Bockius LLP

(57) ABSTRACT

Use of an association of lactobacilli for preparation of a pharmaceutical composition for treatment of vaginosis and vaginitis. Said bacteria association comprises the Lactobacillus brevis and Lactobacillus salivarius subs. salicinius species, possibly in combination with one or more species selected from Lactobacillus salivarius subs. salivarius, Lactobacillus jensenii, Lactobacillus catenaforme, Lactobacillus minutus and Lactobacillus gasseri.

A pharmaceutical composition comprising said association of lactobacilli adapted for treatment of vaginosis and vaginitis.

A method of treating vaginosis and vaginitis based on administration of said pharmaceutical composition.

8 Claims, No Drawings

PHARMACEUTICAL COMPOSITIONS CONTAINING LACTOBACILLI FOR TREATMENT OF VAGINAL INFECTIONS AND RELATED METHOD

Matter enclosed in heavy brackets [ ] appears in the original patent but forms no part of this reissue specification; matter printed in italics indicates the additions made by reissue.

FIELD AND BACKGROUND OF THE INVENTION

The present invention relates to the use of particular species of lactobacilli for preparing pharmaceutical compositions for treatment of vaginal infections, as well as to the pharmaceutical compositions thus prepared, and to methods of treating vaginal infections by administration of said compositions.

Normal vagina and normal uterine neck lodge a variety of bacteria assimilable to those of the gastrointestinal system. These bacteria are frequently involved in non-gonococcus infections of the feminine genital system (such as, for example: vulvovaginal abscesses and abscesses of Bartholin's (or greater vestibular) gland, endometritis, salpingitis, ovary abscesses and pelvic peritonitis).

In the progress of inflammatory pelvic diseases of non-venereal nature, often a mixture of anaerobic and aerobic bacteria is found; such a bacteria range may be responsible of infections after gynecological operations, childbirth, abortion, and has been correlated with use of intrauterine devices for preventing impregnation (IUD).

Bacterial vaginosis is the consequence of a bacterial interaction responsible of substitution at the vagina region of a great number of anaerobic bacteria including Bacteroides, Peptostreptococcus, Peptococcus, Mobiluncus G. vaginalis, for lactobacilli. This syndrome is characterized by a smelly although not particularly irritant secretion. There is only a slight itching and dyspareunia is exceptionally uncommon. Bacterial vaginosis is commonly diagnosed among women that have vaginal trouble, although 50% of women responding to diagnosis criteria for bacterial vaginosis are asymptomatic. Bacterial vaginosis is associated with sexual activity and increases as the number of sexual partners increases; however this affection is not considered as an exclusively sexual-transmission disease.

Although bacterial vaginosis is slightly troublesome, it may predispose to development of more serious infections of the genital system, in particular during pregnancy.

A diagnosis of bacterial vaginosis is given when three of the following four symptoms are encountered:

(1) a homogeneous non-inflammatory vaginal secretion, adhering to vagina walls;

(2) a vaginal fluid having pH greater than 4.5;

(3) indicator cells; and (4) a nauseating smell of the vaginal secretion before or after addition of 10% potassium hydroxide (Whiff's test).

Vaginitis, on the contrary, is characterized by an abnormal vaginal secretion, local irritation and vulvar itch. The above are the symptoms of a local infection due to T. vaginalis, or Candida (above all Candida albicans). Vaginosis and symptomatic vaginitis are associated with diabetes, parathyroid insufficiency, altered defenses of the host organism, corticosteroid treatment, broad-spectrum antibiotic treatment, oral contraceptive drugs and pregnancy. Itch and secretion are the main symptoms of vaginitis due to Candida. Occasionally dyspareunia occurs. Vulva erythema and vulvovaginal thrush can be noticed. For a diagnosis of vaginitis due to Candida the presence of local symptoms is required because usually women can have Candida in the vagina without showing any trouble.

The results of recent studies have encouraged acknowledgment of the important role accomplished by lactobacilli in keeping a normal bacterial equilibrium within the dynamic ecosystems, such as vagina, and for prevention of genital infections caused by pathogenic organisms.

It is well known that many lactobacilli colonize the vagina of wealthy adult women. They propagate using as an energy source the glycogen secreted from the vaginal mucous membrane and compete with the pathogenic agents from the latter, so as to keep the vaginal lumen defended from the attack of other bacteria. Sulfonamides, antibiotics and disinfectant drugs have been mainly used for treatment of the above mentioned diseases (non-specific vaginitis, vaginosis and vulvar itch, for example). In particular, in the most recent years, with the development of many antibiotics, often antibiotic preparations have been administered to patients. Lactobacilli present in the vagina can succumb to administration of these antibiotics. Unfortunately, pathogenic bacteria (Staphylococcus, for example) can acquire a resistance to antibiotics and thus make it difficult to treat these diseases by administering antibiotics.

In U.S. Pat. No. 5,176,911 use of lactobacilli has been proposed in gynecology for treatment of vaginal infections.

This document refers to the following bacteria: Lactobacillus casei, Lactobacillus gasseri, Lactobacillus fermentum, Lactobacillus casei subs. pseudoplantarum and Lactobacillus crispatus, and suggests bacteria concentrations of $10^3$ to $10^{10}$ CFU/g, preferably of about $10^6$ CFU/g.

However, all compositions exemplified in this document contain Lactobacillus casei and/or Lactobacillus fermentum as the essential components, at concentrations of $1\times10^6$ CFU/g. Therefore, practically this document teaches that Lactobacillus casei and/or Lactobacillus fermentum are essential components for preparing pharmaceutical compositions for treatment of vaginal infections and that these compositions are efficient at bacteria concentrations of $1\times10^6$ CFU/g (abbreviation "CFU" means "colony-forming unit").

Pharmaceutical compositions of the known art, made in the form of pessaries or tablets for vaginal use, containing lactobacilli, are not sufficiently efficient in re-establishing the vagina colonization. It is further to note that an important proportion of the bacterial cells dies as a result of the physical impact given at the moment of preparation of pessaries and their number is further reduced when they diffuse in the vagina lumen and their propagation should begin.

Therefore, there is a need to dispose of appropriate species of lactobacilli, or mixtures thereof, and of pharmaceutical compositions containing them, which are free of the drawbacks of the known art compositions.

In particular there is need for pharmaceutical compositions for vaginal use having such good qualities that administration of same to a patient is really beneficial.

In addition, the pharmaceutical composition embodiments should be capable of maintaining the number of lactobacilli being propagated constant and ensuring a continuous and constant action in time of said lactobacilli during diffusion of same in the vaginal lumen.

The Applicants have found that lactobacilli-based pharmaceutical compositions greatly efficient for treatment of vaginal infections can be obtained, provided the following features can be met to the highest possible degree:

(a) the selected lactobacillus strain must have a high affinity towards the vaginal epithelium, i.e. a high capability of adhering to the epithelial cells of the vagina, in that this property enables bacteria interaction with the vagina mucosa under both physiological and pathological conditions (thus performing a competitive action with the pathogenic microorganisms in the epithelial receptor sites) and re-establishment of microflora and optimal pH conditions;

(b) at least one selected lactobacillus strain must have a high capability of producing hydrogen peroxide performing an inhibiting action addressed to the pathogenic microorganisms; and (c) at least one selected lactobacillus strain must be characterized by a high capability of interfering in a competitive manner with adhesion of the Candida albicans to HeLa cells.

SUMMARY OF THE INVENTION

Therefore, it is an object of the present invention to provide lactobacilli-based pharmaceutical compositions meeting the above features to the highest possible degree, and therefore adapted to be efficiently employed for treatment of vaginal infections, such as vaginitis and vaginosis, for example. In this connection the Applicants have found the lactobacilli of the Lactobacillus brevis and Lactobacillus salivarius subs. salicinius species meet the whole of the above three features to a greatly higher degree than other lactobacillus species.

Another object of the present invention is to provide pharmaceutical compositions adapted to vaginal administration comprising lactobacilli made in the form of: liquid compositions, compositions in the form of a cream or ointment and solid compositions in particular in the form of pessaries and tablets.

It is a further object of the invention to provide solid pharmaceutical compositions capable fo releasing lactobacilli carried therein in a differentiated manner in time.

The foregoing and further objects that will become apparent in the progress of the following detailed description are achieved by the present invention the object of which, in a first aspect thereof, is to provide use of an association of lactobacilli of the Lactobacillus brevis and Lactobacillus salivarius subs. salicinius species for preparation of a pharmaceutical composition to be employed through vaginal administration for treatment of vaginal infections such as vaginitis and vaginosis, for example.

In another aspect, it is an object of the present invention to provide said pharmaceutical composition.

In a still further aspect, it is an object of the present invention to provide a method of treating vaginal infections in which said pharmaceutical composition is administered.

DESCRIPTION OF THE PREFERRED EMBODIMENTS

In particular embodiments of the present invention bacteria of the Lactobacillus brevis and Lactobacillus salivarius subs. salicinius species can be used in combination with one or more species of lactobacilli selected from Lactobacillus salivarius subs. salivarius, Lactobacillus jensenii, Lactobacillus catenaforme, Lactobacillus minutus and Lactobacillus gasseri.

Preferably, association of bacteria used in the pharmaceutical composition in accordance with the present invention comprises or consists of Lactobacillus brevis, Lactobacillus salivarius subs. salicinius and Lactobacillus gasseri.

Particular examples of lactobacilli to be used are:

Lactobacillus brevis ATCC 4006 and ATCC 14869

Lactobacillus salivarius subs. salicinius ATCC 11742

Lactobacillus gasseri ATCC 9857

By ATCC it is intended American Type Culture Collection, 12301 Parklawn Drive, Rockville, Ma. 20852, USA.

Preferably, in the association of bacteria employed in accordance with the present invention the bacteria concentration is $10^7$ to $10^{13}$ CFU/g, more preferably $10^8$ to $10^{12}$ CFU/g, most preferably more than $10^9$ to $10^{12}$ CFU/g. Preferably, in said association of bacteria each species is present at a concentration of $10^8$ to $10^{12}$ CFU/g.

The bacterial cultures preferably are in a lyophilized form.

For practical use the pharmaceutical compositions of the invention are prepared in a liquid form (solutions for lavages), in the form of creams or ointments, or in a solid form, i.e. as pessaries or vaginal tablets, packets and the like. The pharmaceutical compositions made in the form of tablets can be of a single layer or two or more layers having differentiated release times.

In particular, the pharmaceutical compositions of the present invention can be prepared in the form of tablets comprising at least two layers, both containing said species of lactobacilli, bound with usual excipients and additives, so that the release velocity of bacteria the outermost layer is greater than the release velocity of bacteria of the innermost layer.

By way of example, the pharmaceutical compositions of the present invention can be prepared in the form of tablets made up of two layers. Such two layers can be made in such a manner that bacteria in the outer layer are released in a lapse of time of 10–25 minutes, about 15–20 minutes for example, whereas bacteria of the inner layer are released subsequently in a lapse of time of 25–50 minutes, about 30–40 minutes for example.

In a preferred embodiment of the present invention, the pharmaceutical compositions also contain a buffer agent capable of maintaining an intervaginal pH stabilized in a gap included between 3 and 5.5 for some hours after administration. The buffer agent is a buffer system consisting of a weak acid selected from any pharmaceutically-acceptable inorganic or organic weak acid, such as boric acid, lactic acid, ascorbic acid, citric acid or acetic acid for example, in combination with the respective sodium salt or another pharmaceutically acceptable salt of the conjugated base of the weak acid used. Preferably, the pH is buffered in a gap of 4.2 to 4.5 and preferably as the buffer agent it is used a buffer system made up of: lactic acid and sodium lactate or ascorbic acid and sodium ascorbate.

Further components or ingredients that can be possibly included in the preparations of the present invention are flavors, menthol, essence of eucalyptus, methyl salicylate or salicylates as topic refreshing agents, hydrocortisone or other antiinflammatory steroids (0.01 to 500 mg/g), antiphlogistic drugs, antimicrobic and moistening agents (EDTA, dodecaethylene glycol monolaurate, etc.), estriol (0.001 to 1 mg/g) and/or other hormonal substances or substances performing a hormonal activity, maize starch or potato starch, vitamins, anti-oxidants, enzymes (hyaluronidase), heparinoids, lycodaine and other topic anesthetics, plant extracts (Belladonna), zinc, calcium and bismuth.

For preparation of water formulations for lavages and irrigations, small bottles are used that are provided with reservoirs containing the lyophilized microorganisms to be dissolved before use in an appropriate liquid medium separately contained in the small bottles. The compositions of the invention are practically free of any toxic character and do not give rise to any systemic absorption, so that administration to pregnant patients is also allowed, as well as in case of an allergy to antimycotic and antibacterial drugs.

According to the hitherto acquired clinical experience, a treatment schedule comprising administration of the composition of the invention in the form of tablets, creams and pessaries to be administered before sleeping, followed by a lavage the next morning is considered as particularly appropriate and efficient.

After describing the present invention in a general manner, the same will be better understood referring it to some specific examples given hereinafter for illustrative purposes only which are not to be intended in a limiting sense.

EXAMPLES

Example 1

Adhesion Lactobacilli to HeLa Cells

By this test there was examined the capability of different strains of Lactobacilli from the American Type Culture Collection (ATCC) to adhere to HeLa cells, a cell line originating from a human carcinoma of the uterine neck. HeLa cells were maintained as monolayer in tissue-culture bottles in MEM (Minimal Essential Medium) with addition of 10% (v/v) fetal bovine serum (FBS). The adhesion reaction was carried out in a multiple-well culture plate for tissues containing a sterile covering slide (24×24 mm) in each well. In each well 1 ml of HeLa cell suspension at a concentration of $1.2\times10^5$ cells/ml was sown and the plates were incubated for 24 hours at 37° C. in a 5% $CO_2$ atmosphere. Before the adhesion test, all bacterial strains were placed in a MRS broth sub-culture (Difco). After a 24 hour incubation at 37° C. under anaerobic conditions (15% $CO_2$) the bacteria were "strengthened" in a new broth and then incubated overnight under the same experimental conditions. An anaerobic environment was obtained by incubating the bacteria in a jar containing specific bags of "Anaerogen" (Oxoid). For the adhesion test, different dilutions of bacterial suspension in MEM were incubated on cell monolayers over one hour at 37° C. under microaerophilic conditions. After several washings in PBS to remove the microorganisms that did not adhere, the cells were set with 0.4 ml of May Grumwald per well for 4 minutes, washed with water-diluted Giemsa for 15 minutes before examination with an optical microscope. The processing concentrations were selected based on the percentage of cells having adhering bacteria and the number of bacteria/cell. The maximum adhesion was obtained at concentrations of $5\times10^9$ bacteria/ml.

The obtained results set forth in Table 1, show that tested lactobacilli were capable of adhering to HeLa cells, showing different adhesion degrees to the host cells. The highest adhesion degrees were found in Lactobacillus brevis and Lactobacillus salivarius subs. salicinius species. Lactobacillus case, in addition to having a low adhesion degree, is invasive and therefore is not adapted for preparation of the pharmaceutical composition of the present invention.

TABLE 1

Adhesion of different lactobacillus strains to HeLa cells.

| Lactobacilli | Bacterial adhesion: No. of adhering bacteria/cell | Bacterial adhesion: % Cells with adhering bacteria | Invasiveness (a) |
|---|---|---|---|
| A) L. salivarius subs. salicinius (ATCC 11742) | 15 | 60 | – |
| B) L. brevis (ATCC 4006) | 35 | 100 | – |
| C) L. brevis (ATCC 14869) | 35 | 100 | – |
| D) L. crispatus (ATCC 33197) | 10 | 45 | +/– |
| E) L. gasseri (ATCC 9857) | 5 | 16 | – |
| F) L. casei (ATCC 8530) | 8 | 19 | + |

(a) + = invasive; +/– = slightly invasive; – = non invasive.

The quantitative bacterial adhesion is expressed as a percentage of 300 randomly selected cells with adhering bacteria and as average number of adhering bacteria per cell.

Example 2

Anti Candida Effect of Lactobacilli

The capability of various lactobacillus species of interfering in a competitive manner with adhesion of the Candida albicans (and therefore on the Candida albicans infectiveness) to HeLa cells was examined.

In order to evaluate the lactobacillus influence on the adhesion level of Mycetes (C. albicans) to host cells, monolayer HeLa cells, grown up in 24-well plates containing sterile covering slides were inoculated with 0.1 ml of a mixture of lactobacilli and C. albicans (two clinical samples isolated from a human vagina referred to in this study as CA2 and CA3, respectively) diluted in PBS at final concentrations of $5\times10^9$ bacteria/ml and $5\times10^8$ Mycetes/ml, respectively. After one hour of incubation at 37° C. under microaerophilic conditions, cells were washed five times in PBS set with May Grunwald and Giemsa. Then slides were controlled with an optical microscope (1000×magnification) and the level of microorganisms adhering to HeLa cells was evaluated. The obtained results, set forth in Table 2, show that all tested lactobacilli are capable of reducing adhesion of C. albicans to HeLa cells, the highest inhibitory-activity degree being shown by L. brevis ATCC 4006, which produced a reduction of about 50% in the number of cells with adhered Candida and reduced the number of Mycetes/cell to about half the control number.

TABLE 2

Competitive exclusion of C. albicans adhesion to HeLa cells by lactobacilli

| Microorganism | % cells with: Mycetes | % cells with: bacteria | Average No. of microorganisms/cell: Mycetes | Average No. of microorganisms/cell: bacteria |
|---|---|---|---|---|
| CA2 | 68 | | 5 | |
| CA3 | 61 | | 7 | |
| A) L. salivarius subs. salicinius ATCC 11742 | | 54 | | 10 |

TABLE 2-continued

Competitive exclusion of C. albicans adhesion to HeLa cells by lactobacilli

| Microorganism | % cells with | | Average No. of microorganisms/cell | |
|---|---|---|---|---|
| | Mycetes | bacteria | Mycetes | bacteria |
| B) L. bervis ATCC 4006 | | 95 | | 20 |
| C) L. gasseri ATCC 9857 | | 15 | | 6 |
| D) L. casei ATCC 8530 | | 13 | | 8 |
| CA2 + A | 52 | 55 | 3 | 10 |
| CA3 + A | 43 | 54 | 3 | 11 |
| CA2 + B | 44 | 99 | 3 | 20 |
| CA3 + B | 34 | 99 | 2 | 20 |
| CA2 + C | 48 | 15 | 4 | 6 |
| CA3 + C | 57 | 16 | 5 | 5 |
| CA2 + D | 61 | 12 | 5 | 7 |
| CA3 + D | 58 | 12 | 5 | 7 |

For the competitive-exclusion test, lactobacilli and Mycetes were used at a final concentration of $5\times10^9$/well and $5\times10^9$/well, respectively.

Example 3

Production of Hydrogen Peroxide by Lactobacilli

The capability of five lactobacilli species of producing $H_2O_2$ was examined. Bacteria were placed for culture on an agar-agar plate with tetramethylbenzidine. After three days of incubation at 37° C. in a jar under anaerobic conditions, the agar-agar plates were exposed to the air. In this way, the peroxidase present in the culture medium reacts with the $H_2O_2$ produced by lactobacilli. The subsequent oxidation of tetramethylbenzidine is revealed by a blue pigmentation of the $H_2O_2$-producing colonies. The obtained results, set forth in Table 3, show that L. salivarius subs. salicinius ATCC 11742 and L. gasseri ATCC 3857 were positive to $H_2O_2$.

L. casei ATCC 8530 did not show any positivity. The other tested strains were devoid of any reaction. These results show that no correlation exists between the $H_2O_2$ production by lactobacilli and the competitive exclusion of the C. albicans adhesion to HeLa cells by bacteria.

TABLE 3

Production of hydrogen peroxide by lactobacilli

| Lactobacilli | Production of $H_2O_2$ |
|---|---|
| A) Lactobacillus salivarius subs. salicinius (ATCC 11742) | + |
| B) Lactobacillus brevis (ATCC 4006) | – |
| C) Lactobacillus brevis (ATCC 14869) | – |
| D) Lactobacillus gasseri (ATCC 3857) | + |
| E) L. casei (ATCC 8530) | – |

+ = blue pigmentation of all bacteria colonies.
+/– = light blue pigmentation.
– = no pigmented colony.

For illustrative purposes, but not in a limiting sense, some examples of preferred pharmaceutical compositions are reproduced hereinafter, which compositions are intended for preparing tablets, pessaries, creams and liquid solutions for vaginal administration of a microbiotic-culture lyophilized product consisting of an association of several microbic species.

Examples of Vaginal Reparations

Example 4

Unitary composition for preparing quick-release slightly effervescent tablets comprising carriers and a microbic-culture lyophilized product ($1\times10^{10}$ CFU/g) consisting of an association of L. brevis ATCC 4006 and L. salivarius subs. salicinius ATCC 11742 (in a 1:1 ratio):

| | |
|---|---|
| Microbic-culture lyophilized product | 500 mg |
| Lactose | 350 mg |
| Maize starch | 200 mg |
| Adipic acid | 67 mg |
| Sodium bicarbonate | 67 mg |
| Magnesium stearate | 11 mg |
| Stearic accid | 3 mg |
| Colloidal silica | 2 mg |

For preparation of tablets having the above composition, previous preparation of a granulate or pellets is required.

The lubricated pallets are then added with 500.0 g of said microbic-culture lyophilized product previously sieved on a 300 μm mesh, and mixed again for 15 minutes. Pellets thus obtained are submitted to the subsequent compression operation using a rotary compressing machine provided with shaped punches of oval form, so that vaginal-use tablets are obtained of an average weight of 1200 mg.

The obtained tablets have a disgregating time of about 15 minutes, by use of the apparatus described in the Farmacopea Ufficiale Italiana.

Example 5

Unitary composition for preparing slow-release tablets comprising carriers and the same microbic-culture lyophilized product as in Example 4:

| | |
|---|---|
| Microbic-culture lyophilized product | 500 mg |
| Mannitol | 560 mg |
| Hydroxipropyl methylcellulose | 80 mg |
| Talc | 18 mg |
| Magnesium stearate | 19 mg |
| Colloidal silica | 3 mg |

The microbic-culture lyophilized product is calibrated by forcing the spongy mass onto a 270 μm mesh; the sieved product is added with mannitol, previously sieved on a 279 μm mesh, hydroxipropyl methylcellulose, talc, magnesium stearate and colloidal silica. The whole mass is mixed for 30 minutes in a Turbula T2A type mixer for powders. The thus obtained mixture is submitted to the subsequent compression operation, using a rotary compressing machine provided with shaped punches of oval form thus obtaining vaginal-use tablets of an average weight of 1200 mg.

The obtained tablets have a disgregating time of about 30 minutes, by use of the apparatus described in the Farmacopea Ufficiale Italiana.

Example 6

Preparation of two-layer (one quick-release layer and one slow-release layer) tablets comprising carriers and the same microbic-culture lyophilized product as in Example 4.

Unitary composition for preparation of the quick-release layer (it is a slightly effervescent layer):

| | |
|---|---|
| Microbic-culture lyophilized product | 250 mg |
| Lactose | 240 mg |
| Maize starch | 41 mg |
| Adipic acid | 30 mg |
| Sodium bicarbonate | 30 mg |
| Magnesium stearate | 6 mg |
| Stearic accid | 2 mg |
| Colloidal silica | 1 mg |

Unitary composition for preparation of the slow-release layer:

| | |
|---|---|
| Microbic-culture lyophilized product | 250 mg |
| Mannitol | 280 mg |
| Hydroxipropyl methylcellulose | 50 mg |
| Talc | 9 mg |
| Magnesium stearate | 10 mg |
| Colloidal silica | 1 mg |

Pellets to be used for the quick-release layer are prepared following the process described in Example 4; mixture to be used for the low-release layer is prepared following the process described in Example 5.

The described pellets for the quick-release layer and the described mixture for preparation of the slow-release layer are loaded in two distinct loading hoppers of an appropriate compressing machine, adapted to produce two-layer tablets (Manesty Layer Press type) provided with punches of curved oval form.

The machine is such adjusted that two-layer tablets are obtained of an overall average weight of 1200 mg consisting of 2 layers of 600 mg each and each containing 250 mg of the microbic-culture lyophilized product.

The obtained two-layer tablets, submitted to the disgregaing test using the apparatus described in the Farmacopea Ufficiale Italiana, have a disgregating time of about 15 minutes for the quick-release layer and 30–40 minutes for the slow-release layer.

Example 7

Active ingredient: 1 g of the same microbic-culture lyophilized product as in Example 4.

Excipients: 2.5 g of semisynthetic glycerides and potato starch.

Example 8

VAGINAL CREAM (tube of 10 g)

Active ingredient: 1 g of the same microbic-culture lyophilized product as in Example 4.

Excipients: hydrogenated lanolin (2 g), Vaseline oil (2 g), dimethyl polysiloxane (3 g), $SiO_2$ (4 g).

Example 9

SMALL BOTTLES WITH RESERVOIR

Each small bottle contains:

a) Reservoir: 2 g of the same microbic-culture lyophilized product as in Example 4.

b) Small bottle (10 ml): glycerol 3 g and water in a sufficient amount to 10 ml.

Examples 10 to 15

Examples 4 to 9 were repeated following the same modalities as specified in said Examples respectively, with the only difference that a microbic-culture lyophilized product was used (concentration $1\times10^{10}$ CFU/g) which consisted of L. brevis ATCC 14869, L. salivarius subs. salicinius ATCC 11742 and L. gasseri ATCC 9857 species in a 1:1:1 ratio.

All pharmaceutical preparations obtained in Examples 4 to 15 have proved to be very efficient in treating patients suffering from vaginosis and vaginitis.

What is claimed is:

1. A composition comprising lactobacilli of the Lactobacillus brevis and Lactobacillus salivarius subs. salicinius species, in the form of pessaries or vaginal tablets comprising at least two layers, both layers containing said species of lactobacilli, in bound form, so that the release velocity of bacteria of the outermost layer is greater than the release velocity of bacteria of the innermost layer.

2. The composition as claimed in claim 1, wherein said composition further comprises one or more species of lactobacilli selected from Lactobacillus salivarius subs. salivarius, Lactobacillus jensenii, Lactobacillus catenaforme, Lactobacillus minutus and Lactobacillus gasseri.

3. The composition as claimed in claim 2, wherein said lactobacilli consist of the Lactobacillus brevis, Lactobacillus salivarius subs. salicinius and Lactobacillus gasseri species.

4. The composition as claimed in claim 1, wherein said lactobacilli are present at a concentration of $10^7$ to $10^{13}$ CFU/g.

5. A method of treatment of a vaginal infection, comprising administering through the vagina a composition comprising lactobacilli of the Lactobacillus brevis and Lactobacillus salivarius subs. salicinius species, in the form of pessaries or vaginal tablets comprising at least two layers, both layers containing said species of lactobacilli, in bound form, so that the release velocity of bacteria of the outermost layer is greater than the release velocity of bacteria of the innermost layer.

6. The method of claim 5, said composition further comprises one or more species of lactobacilli selected from Lactobacillus salivarius subs. salivarius, Lactobacillus jensenii, Lactobacillus catenaforme, Lactobacillus minutus and Lactobacillus gasseri.

7. The method of claim 6, wherein said lactobacilli consist of the Lactobacillus brevis, Lactobacillus salivarius subs. salicinius and Lactobacillus gasseri species.

8. The method of claim 5, wherein said lactobacilli are present at a concentration of $10^7$ to $10^{13}$ CFU/g.

* * * * *